United States Patent [19]

Rogers et al.

[11] 4,284,570
[45] Aug. 18, 1981

[54] ANTIBACTERIAL COMPOUNDS

[75] Inventors: Norman H. Rogers, Rudgwick; Peter J. O'Hanlon, Redhill, both of England

[73] Assignee: Beecham Group Limited, England

[21] Appl. No.: 85,894

[22] Filed: Oct. 18, 1979

Related U.S. Application Data

[62] Division of Ser. No. 21,712, Mar. 19, 1979, Pat. No. 4,248,887.

[30] Foreign Application Priority Data

Apr. 21, 1978 [GB] United Kingdom .............. 15807/78

[51] Int. Cl.³ ........................................... C07D 309/10
[52] U.S. Cl. ............................................. 260/345.7 R
[58] Field of Search .................................. 260/345.7 R

[56] References Cited

U.S. PATENT DOCUMENTS

| 4,102,901 | 7/1978 | Luk et al. ...................... 260/345.7 R |
| 4,102,904 | 7/1978 | Luk et al. ...................... 260/345.7 R |

FOREIGN PATENT DOCUMENTS 3069 7/1979 European Pat. Off. .............. 260/345.7

*Primary Examiner*—Nicky Chan
*Attorney, Agent, or Firm*—Jacobs & Jacobs

[57] ABSTRACT

This invention relates to antibacterial compounds and in particular to a class of esters which have antibacterial activity against certain Gram-positive and Gram-negative organisms, and also possess antimycoplasmal activity. The compounds are therefore of value in the treatment of human and veterinary infections.

1 Claim, No Drawings

ANTIBACTERIAL COMPOUNDS

CROSS REFERENCE

This is a division of Ser. No. 21,712 filed Mar. 19, 1979, now U.S. Pat. No. 4,248,887.

European Patent Application No. 78300530.9 discloses a compound of formula (I):

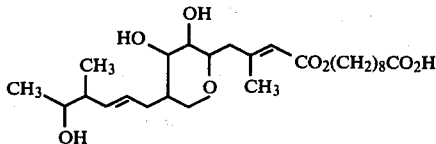

which is obtainable from the bacterium *Pseudomonas fluorescens*. The compound of formula (I) having the tri-substituted double bond in the E-configuration is referred to as "pseudomonic acid C". It has now been found that the allylic carboxylic acid moiety of this molecule is useful for preparing other esterified derivatives, which are also antibacterially active.

Accordingly, the present invention provides a compound of formula (II):

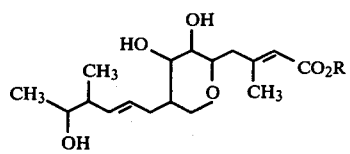

wherein R is hydrogen, a salt-forming ion or pharmaceutically acceptable ester-forming radical, provided that R is not a group of formula $-(CH_2)_8CO_2H$, or a salt or ester thereof.

The compound (II) of this invention incorporates a tri-substituted double bond and may therefore exist in both the E (natural) and Z (or iso) geometrical forms. It is to be understood that both geometrical isomers of the compound of formula (II) are included within the scope of this invention, as well as mixtures of the two isomers. However, because pseudomonic acid C has the tri-substituted double bond in the E-configuration, it is preferable to employ the corresponding isomer of compound (II).

The compound of formula (II) wherein R is hydrogen and the tri-substituted double bond is in the E-configuration, we have designated "monic acid C" and it will be referred to as such in this specification. The corresponding Z-isomer is termed "isomonic acid C".

The di-substituted double bond in compound (II) is in the trans-configuration.

When the group R is a salt-forming radical, the salts may be pharmaceutically acceptable, but need not be, as the chief utility of a compound (II) where R is other than an ester-forming radical, is as an intermediate. Suitable salts of the compound include metal salt, e.g. aluminium, alkali metal salts, such as sodium or potassium, alkaline earth metal salts, such as calcium or magnesium, and ammonium or substituted ammonium salts for example those with lower alkyl-amines such as triethylamine, hydroxy-lower alkylamines such as 2-hydroxyethylamine, bis(2-hydroxyethyl)-amine, or tri-(2-hydroxyethyl)-amine, cycloalkylamines such as bicyclohexylamine, or with procaine, dibenzylamine, N,N-dibenzyl-ethylene-diamine, 1-ephenamine, N-ethyl-piperidine, N-benzyl-β-phenethyl-amine, dehydroabietylamine, N,N'-bis-dehydroabietylethylenediamine, or bases of the pyridine type such as pyridine, collidine, or quinoline.

Suitable ester-forming radicals for the group R include (a) $C_{1-20}$ alkyl, $C_{2-8}$ alkenyl or $C_{2-8}$ alkynyl each of which may be optionally substituted by $C_{3-7}$ cycloalkyl, halogen, carboxy, $C_{1-6}$ alkoxycarbonyl, carbamoyl, aryl, heterocyclyl, hydroxy, $C_{1-6}$ alkanoyloxy, amino,- mono- and di-$(C_{1-6})$alkylamino;

(b) $C_{3-7}$ cycloalkyl optionally substituted with $C_{1-6}$ alkyl;

(c) aryl;

(d) heterocyclyl.

The term "aryl" includes phenyl and naphthyl optionally substituted with up to five halogen, $C_{1-6}$ alkyl, $C_{1-6}$ alkoxy, halo ($C_{1-6}$) alkyl, hydroxy, amino, carboxy, $C_{1-6}$ alkoxycarbonyl, or $C_{1-6}$ alkoxycarbonyl-$(C_{1-6})$-alkyl groups.

The term "heterocyclyl" includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-$(C_{1-6})$-alkyl, hydroxy, amino, carboxy, $C_{1-6}$ alkoxycarbonyl, $C_{1-6}$ alkoxycarbonyl-$(C_{1-6})$-alkyl, aryl or oxo groups.

One suitable substituted alkyl group for the group R has the formula (III):

wherein n is an integer from 1 to 7 or 9 to 20 and $R^1$ is hydrogen or a pharmaceutically acceptable salt-forming ion or $C_{1-6}$ alkyl.

Another sub-class of esters of formula (II) comprises those compounds wherein the group R has the formula (IIIA):

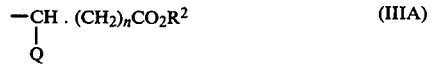

wherein n is zero or 1 to 20, $R^2$ is $C_{1-6}$ alkyl, and Q represents phenyl, $C_{1-6}$ alkyl, $C_{3-7}$ cycloalkyl, $C_{1-6}$ alkoxycarbonylmethyl, benzyl, trifluoromethylbenzyl, halobenzyl.

Preferably, within formula (IIIA) n is zero or 1 to 3, $R^2$ is methyl and Q is phenyl, methyl, iso-propyl, n-hexyl, cyclohexyl, methoxycarbonylmethyl, benzyl, 3-trifluoromethylbenzyl.

Thus the group R in compound (II) may be for example $C_{1-6}$ alkyl, in particular, methyl, ethyl n- or iso-propyl, n-, sec-, iso- or tert-butyl; halo-$(C_{1-6})$-alkyl such as trifluoromethyl, 2-chloroethyl, 2,2,2-trichloroethyl; aminoalkyl groups such as aminoethyl, 2-aminoethyl; hydroxymethyl, 2-hydroxyethyl; phenyl; substituted phenyl; a benzyl group; or a group of formula (III) wherein n is an integer from 1 to 7.

A further sub-class of esters of formula (II) comprises those in which R represents $C_{1-10}$ alkyl, hydroxy-$(C_{1-10})$-alkyl, and $C_{2-8}$ alkenyl. Examples of such R groups include methyl, ethyl, isobutyl, 6-hydroxyhexyl, and allyl (i.e. prop-2-enyl).

Other specific examples of the group R include: $C_{7-20}$ alkyl groups such as heptyl, octyl, nonyl, decyl and dodecyl; cyclopropyl, cyclopropylmethyl, cyclopentyl, cyclohexyl, methoxycarbonylmethyl, 2-methoxycarbonylethyl, 3-methoxycarbonylpropyl, 4-methoxycarbonyl-n-butyl, 5-methoxycarbonyl-n-pentyl, 6-methoxycarbonyl-hexyl, 7-methoxycarbonyl-n-heptyl, 10-methoxycarbonyldecyl, carbamoylmethyl, benzyl, 2,4,6-trichlorophenyl, pentachlorophenyl, o-, m- or p-methylphenyl, o-, m- or p-methoxycarbonylphenyl, 2- or 3- or 4-pyridyl, prop-2-ynyl, 2-dialkylaminoethyl, or 3-methoxycarbonylprop-2-enyl.

The esters of monic acid C, i.e. compound (II) in which R is an ester-forming radical, have antibacterial activity. They have particularly high activity against *Haemophilus influenzae, Neisseria catarrhalis* and Mycoplasma sp, and are therefore of value in the treatment of respiratory and venereal diseases, and of mycoplasma-induced human and veterinary diseases.

In humans the infections against which esters of monic acid C may be particularly useful include venereal disease. Because the structure is not a β-lactam antibiotic the compounds are effective against β-lactamase-producing strains of *N. gonorrhoeae*, against which standard treatments such as penicillin and cephalosporin antibiotics would not be useful. Esters of monic acid C may also be effective in the treatment of respiratory infections such as chronic bronchitis and bacterial meningitis; non-specific urethritis and pneumonia. In animals they may be employed generally as a growth promoter or for the treatment of mastitis in cattle and for treatment of mycoplasma infections in animals such as turkeys, chickens and pigs.

The esters of monic acid C are also particularly useful in the treatment of pneumonia in animals such as pigs, calves and sheep, because they also have activity against the bacterium Pasteurella multocida which often causes respiratory complications in case of this disease.

This invention also provides a pharmaceutical or veterinary composition which comprises a compound of formula (II) wherein R is an ester-forming radical, together with a pharmaceutically or veterinary acceptable carrier or excipient.

The compositions may be formulated for administration by any route, and would depend on the disease being treated. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non aqueous vehicles (which may include edible oils), for example almond oil fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability the composition can be frozen after filling into the vial and water removed under vacuum. The dry lyophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 50–500 mg., of the active ingredient. The dosage as employed for adult human treatment will preferably range from 100 mg to 3 g, per day, for instance 250 mg to 2 g, per day, depending on the route and frequency of administration.

Alternatively an ester of monic acid C may be administered as part of the total dietary intake. In this case the amount of compound employed may be less that 1% by weight of the diet and in preferably no more than 0.5% by weight. The diet for animals may consist of normal foodstuffs to which the compound may be added or it may be added to a premix.

The present invention also provides a process for the preparation of a compound of formula (II) as defined above which process comprises reacting a compound of formula (IV) or a hydroxyl-protected derivative thereof:

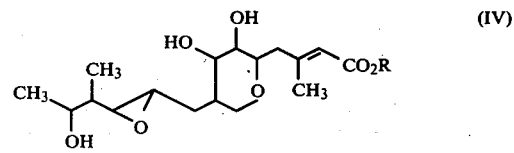

wherein R is as defined with respect to formula (II) above; with a reagent which converts an epoxide to an olefin; and optionally thereafter carrying out one or more of the following steps:

(i) forming a salt of a compound of formula (II) produced in which R is hydrogen;

(ii) esterifying a compound of formula (II) produced in which R is hydrogen or a salt-forming ion or trans-esterifying a compound of formula (II) produced in which R is an ester forming radical; or (iii) hydrolysing a compound of formula (II) produced in which R is an ester-forming radical; and (iv) removing any hydroxyl-protecting group.

The compounds of formula (IV) are disclosed in our West German OLS Nos. 2,726,618 and 2,726,619. The E-form of compound (IV) in which R is hydrogen is referred to as "monic acid A".

A number of reagents for converting an epoxide to an olefin are known in the literature, and the particular reagent of choice for the process of the present invention is a matter of trial and error. Some such reagents are more suitable than others for this purpose.

Some generally applicable methods are as follows:

(a) Potassium selenocyanate in an alkanol/water solvent (see JCS Chem. Comm., 1975, 1216; JCS 1949, 278);

(b) Lower valent tungsten halides; for example $WCl_6$/butyl lithium (see J. Amer. Chem. Soc. 1972, 94, 6538);

(c) $Ph_3P=Se$/trifluoroacetic acid (see JCS Chem. Comm. 1973, 253);

(d) Trifluoroacetyl iodide/sodium iodide (see J. Org. Chem., 1978, 43, 1841);

(e) Diphosphorus tetraiodide (see Synthesis, 1978, 905).

Other methods are described in the following references:

J. Amer. Chem. Soc., 1973, 95, 2697

Tet. Letts, (17) 1976, 1395

Ber., 1955, 88, 1654

J. Org. Chem., 1958, 22, 1118

It has been found that one convenient method is the use of potassium selenocyanate.

Suitable solvents for use with potassium selenocyanate include mixtures of water with alkanols, in particular $C_1$ to $C_{20}$ alkanols. It has been found that higher yields of the compound of formula (II) are achieved if an alcohol is employed with a large, in particular branched or cyclic, alkyl group. Specific alcohols include tert-amyl alcohol, 2-ethyl-n-butanol, and cyclohexyl alcohol. The reaction is generally performed at elevated temperatures, suitably at about the boiling point of the solvent employed. The time for which the reaction is performed depends on the temperature of the reaction, and therefore on the solvent. Generally a time of from 1 to 9 days is suitable.

Another suitable method for converting the epoxide of pseudomonic acid A, or a salt or ester thereof into an olefin, comprises treatment with trifluoroacetyl iodide and sodium iodide. The trifluoroacetyl iodide may be prepared in situ from trifluoroacetic anhydride. The reaction is suitably conducted at ambient temperature for from about 10 to 36 hours, suitably about 24 hours.

When the free acid or salt of compound (II) is required it may be convenient to employ an ester of compound (IV) for the above process, which ester is a carboxyl-protecting group. Suitable carboxyl-protecting groups would depend on the reaction conditions for de-epoxidation and include the 2,2-trichloroethyl ester, (which may be removed with zinc in a lower alcohol, especially methanol) phenyl, pentachlorophenyl, benzyl, and t-butyl ester groups. Other suitable carboxyl-protecting groups are silyl groups such as trimethylsilyl or 5-butyldiphenylsilyl. A preferred silylating agent is N,O-bis (trimethyl-silyl) acetamide, which produces the trimethyl-silyl derivative of the acid.

Prior to the above process of this invention, it may be desirable, in some case, to protect the hydroxyl groups in compound (IV) using conventional hydroxyl-protecting groups. Suitable groups include silyl groups. Particularly suitable hydroxyl-protecting groups include trimethylsilyl, t-butyldimethylsilyl, methylthiomethyl. A preferred hydroxyl-protecting group is trimethylsilyl, as it is readily removed on completion of the reaction. Alternatively, for some de-epoxidation reactions it is possible to protect the hydroxyl groups with other ester radicals which may be removed by chemical or enzymatic means. Examples include p-nitrobenzoate, methoxyacetate, phenoxyacetate, trifluoroacetate, each of which may be removed under mild basic conditions such as aqueous ammonia; or potassium carbonate in aqueous methanol.

It is also possible to protect the glycol moiety in compound (IV), and suitable reagents for forming such a hydroxyl-protecting group include compounds of formula (V):

wherein $R^1$ is hydrogen or a $C_{1-6}$ alkyl group and $R^2$, $R^3$ and $R^4$ independently represent a $C_{1-6}$ alkyl group.

The group $R^1$ may be for example hydrogen, methyl, ethyl, n- or iso-propyl. Most suitably, $R^1$ represents hydrogen so that the compound of formula (V) is a trialkyl orthoformate.

Groups $R^2$, $R^3$, and $R^4$ may be for example, methyl, ethyl, n- or iso-propyl, n-, iso-, sec- or tert-butyl. Preferably $R^2$, $R^3$, and $R^4$ are all the same and each represents a methyl group.

Other glycol protecting groups include those wherein the glycol moiety is converted to the structure:

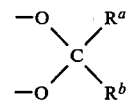

where $R^a$ and $R^b$ are hydrogen, $C_{1-6}$ alkyl, or phenyl. Preferably $R^a$ and $R^b$ are both methyl, i.e. the group is the isopropylidene (or "acetonide") group. This group may be introduced onto compound (IV) or its salt or ester by reaction with 2,2-dimethoxypropane, and removed by treatment with acetic acid.

The hydroxy-protecting group may be removed by a conventional method for the particular hydroxyl-protecting group.

When an ester of compound (II) is required, the esterification or trans-esterification step, step (ii) above may be performed by any conventional method. For example, esterification may be carried out by reaction of the acid, or a salt thereof:

(a) with the appropriate halide, sulphate or alkanesulphonate of the alcohol in the presence of a solvent such as acetone, dimethylsulphide or dimethylsulphoxide and calcium, or potassium carbonate or with the halide in the presence of hexamethyl phosphoramide; or (b) by phase transfer catalysis methods with the halide and/or sulphate of the alcohol in aqueous and/or organic solution in the presence of a quaternary ammonium salt such as tetrabutyl ammonium bisulphate or halide, or benzyltrimethyl-ammonium halide; or (c) with a diazoalkane.

Conventional trans-esterification methods include, for example reaction of an ester of formula (II) with the appropriate alcohol in the presence of a catalyst such as the sodium salt of the alcohol, or dry hydrogen chloride, p-toluenesulphonic acid, or potassium cyanide.

The hydrolysis of an ester of compound (II) (step (iii) above) may be chemical hydrolysis, for example by alkaline hydrolysis.

This invention also provides a process for the preparation of a compound of formula (II) as defined above which process comprises either hydrolysis (for a compound where R=H) or trans-esterification (for a compound where R is an ester-forming radical) of a compound of formula (I) above or a salt of ester thereof, and optionally thereafter carrying out one or more of the following steps:

(i) forming a salt of a compound of formula (II) produced in which R is hydrogen;

(ii) esterifying a compound of formula (II) produced in which R is hydrogen or a salt-forming ion or trans-esterifying a compound of formula (III) produced in which R is an ester-forming radical; or (iii) hydrolysing a compound of formula (II) produced in which R is an ester-forming radical.

The hydrolysis or trans-esterification process may be carried out by conventional means, such as those described above.

The hydrolysis is preferably carried out under alkaline conditions, for example in the presence of sodium or potassium hydroxide. Under these conditions it is not normally necessary to protect the hydroxyl groups because compounds of formula (II) do not rearrange in alkaline solution.

The compound of formula (I) employed is suitably pseudomonic acid C or a lower alkyl ester thereof such as methyl pseudomonate C.

The following Examples illustrate this invention.

EXAMPLE 1

Monic Acid C from Pseudomonic Acid C

Pseudomonic acid C (80 mgs) was dissolved in 0.1 M sodium hydroxide (20 ml) and stirred overnight at room temperature. After evaporation to low volume the solution was adjusted to pH 2 (5 M HCl), saturated with sodium chloride and extracted with ethyl acetate. The combined extracts were dried (MgSO$_4$) then evaporated to dryness and chromatographed on silica (2 g) eluting with gradient of 0 to 8% methanol/chloroform. Fractions containing pure product (by hplc and tlc) were combined to give monic acid C (40 mgs, 74%), $\nu_{max}$ (KBr) 3400 (broad) 1692 (broad), 1644, 1238, 975 cm$^{-1}$; $\lambda_{max}$ (EtOH) 218 nm ($\epsilon$9679); $\delta_H$ (CD$_3$OD) 0.97 (3H, d, J 8 Hz, CH$_3$-17), 1.08 (3H, d, J 7 Hz, CH$_3$-14), 2.13 (3H, s, CH$_3$-15), 5.4 (2H, m, H-10, H-11), 5.67 (1H, s, H-2); $\delta_C$ (CD$_3$OD) 170.2 (Cl), 159.0 (C3), 135.8, 129.7 (C10, C11), 118.6 (C2), 76.2 (C5), 72.5 (C7), 71.6 (C13), 70.0 (C6), 65.8 (C16), 45.3 (C12), 44.1 (C4), 43.7 (C8), 33.7 (C9), 20.4 (C14), 19.3 (C15), 16.7 (C17). (Found: 284.1624. C$_{16}$H$_{28}$O$_6$ M.+—C$_2$H$_4$O requires 284.1623).

EXAMPLE 2

Monic Acid C from Methyl Pseudomonate C

Methyl pseudomonate C (0.85 g) was dissolved in methanol (30 ml), diluted with M sodium hydroxide (10 ml) and water (40 ml) then stirred at 70° C. for 3 hours. After cooling and evaporation to dryness the residue was dissolved in water (15 ml) saturated with sodium chloride and layered with ethyl acetate. The pH was then adjusted to 2.5 and the organic layer was separated then the aqueous layer further extracted with ethyl acetate (5×20 ml). The combined organic layers were dried (MgSO$_4$) then evaporated to an oil which was chromatographed on silica (10 g) eluting with gradient of 0 to 6% methanol/chloroform. The fractions containing pure product (by hplc and tlc) were combined and evaporated to give monic acid C (340 mgs, 57%).

EXAMPLE 3

Sodium Monate C

Monic acid C (132 mgs) was dissolved in water (10 ml) and treated with sodium bicarbonate (34 mgs, 1 eq), in water (2 ml). After stirring for half an hour the solution was evaporated to dryness and the residue dried in vacuo over phosphorus pentoxide. The salt was dissolved in a minimum quantity of ethanol and added dropwise to sodium dry ether (50 ml) then sodium monate C filtered off and dried (140 mgs, 100%), $\nu_{max}$ (KBr) 3400 (broad) 1645, 1545 (broad), 1407, 973 cm$^{-1}$, $\lambda_{max}$ (EtOH) 220 nm ($\epsilon$7,630); $\delta_H$ (CD$_3$OD) 0.98 (3H, d, J 7 Hz, CH$_3$-17), 1.08 (3H, d, J 7 Hz, CH$_3$-14), 2.05 (3H, d, J 1 Hz, CH$_3$-15), 5.40 (2H, m, H-10, H-11), 5.73 (1H, m, H-2); $\delta_C$ (CH$_3$OD) 176.9 (C1), 145.6 (C3), 135.7, 129.6 (C10, C11), 126.3 (C2), 76.6 (C5), 72.0 (C7), 71.6 (C13), 70.0 (C6), 65.5 (C16), 45.2 (C12), 43.4 (C8), 42.1 (C4), 33.6 (C9), 20.2 (C14), 18.9 (C15), 16.5 (C17).

EXAMPLE 4

Methyl Monate C

A solution of methyl monate A (0.461 g), potassium selenocyanate (0.566 g) in methanol-water (9:1, 20 ml) was heated under reflux for 9 days. The mixture was cooled, filtered to remove black selenium and the filtrate concentrated in vacuo to remove the methanol. The filtrate was saturated with sodium chloride and extracted several times with ethyl acetate. The latter was washed with saturated brine, dried (MgSO$_4$) and evaporated to an oil (0.324 g) which was chromatographed on silica (10 g) eluting with gradient of methanol/chloroform 0 to 5%. The fractions containing pure methyl monate C were collected and evaporated to an oil (53 mgs, 12%), $\nu_{max}$ (CDCl$_3$) 3500, 1710, 1650, 1440, 1150 cm$^{-1}$, $\lambda_{max}$ (EtOH) 221 nm ($\epsilon$12,000); $\delta_H$ (CDCl$_3$) 0.97 (3H, d, CH$_3$-17), 1.14 (3H, d, CH$_3$-14), 2.18 (3H, s, CH$_3$-15) 3.62 (3H, s, OCH$_3$), 5.4 (2H, m, H-10, H-11), 5.72 (1H, m, H-2); $\delta_C$ (CDCl$_3$) 167.2 (C1), 157.4 (C3), 134.4, 129.3 (C10, C11), 117.1 (C2), 74.8 (C5), 71.3 (C13), 70.3 (C7), 68.9 (C6), 64.9 (C16), 50.9 (OCH$_3$), 44.6 (C12), 43.0 (C4), 41.9 (C8), 32.4 (C9), 20.4 (C14), 19.2 (C15), 16.6 (C17).

EXAMPLE 5

Ethyl Monate C and Isomonate C

Ethyl monate A (2 g) and potassium selenocyanate (2.32 g) in ethanol-water (9:1, 65 ml) were refluxed for 7 days. After filtering off the precipitated selenium the filtrate was evaporated to remove the solvent and the residue dissolved in ethyl acetate (50 ml) and brine (20 ml). The organic layer was separated and washed with brine (20 ml) then dried (MgSO$_4$). The solution was evaporated in vacuo to an oil which was chromatographed on silica (25 g) eluting with gradient of 0 to 6% methanol/chloroform to give two products. The major product was ethyl monate C (370 mgs, 19%), m.p.

96.5°–97.5° C. $\nu_{max}$ (CHCl$_3$) 3420 (broad), 1710, 1645, 980 cm$^{-1}$; $\lambda_{max}$ (EtOH) 222 nm ($\epsilon$11,600); $\delta_H$ (CDCl$_3$) 0.99 (3H, d, J 7 Hz, C$\underline{H}_3$-17), 1.14 (3H, d, J 6 Hz, C$\underline{H}_3$-14), 1.27 (3H, t, OCH$_2$C$\underline{H}_3$), 2.20 (3H, d, J 1 Hz, C$\underline{H}_3$-15), 4.13 (2H, q, OC$\underline{H}_2$), 5.44 (2H, m, $\underline{H}$-10, $\underline{H}$-11), 5.76 (1H, m, $\underline{H}$-2); $\delta_C$ (CDCl$_3$) 166.9 (C1), 157.0 (C3), 134.4, 129.3 (C10, C11), 117.5 (C2), 74.8 (C5), 71.3 (C13), 70.3 (C7), 68.9 (C6), 64.9 (C16), 59.6 (OCH$_2$CH$_3$), 44.6 (C12), 43.1 (C4), 42.0 (C8), 32.4 (C9), 20.4 (C14), 19.2 (C15), 16.6 (C17), 14.3 (OCH$_2$CH$_3$). Found: C, 64.2; H, 9.3; C$_{19}$H$_{32}$O$_3$ requires: C, 64.0; H, 9.1%. The minor product was ethyl isomonate C (130 mgs 7%) $\nu_{max}$ (CHCl$_3$) 3420 (broad), 1728, 1690, 1450 and 975 cm$^{-1}$; $\lambda_{max}$ (EtOH) 222 nm ($\epsilon$8380); $\delta_H$ (CDCl$_3$) 0.99 (3H, d, J 6 Hz, C$\underline{H}_3$-17), 1.14 (3H, d, J-7 Hz, C$\underline{H}_3$-14), 1.34 (3H, t, OCH$_2$C$\underline{H}_3$), 2.00 (3H, s, C$\underline{H}_3$-15), 4.14 (2H, q, OC$\underline{H}_2$CH$_3$), 5.45 (2H, m, $\underline{H}$-10, $\underline{H}$-11), 5.80 (1H, m, $\underline{H}$-2); $\delta_C$ (CDCl$_3$) 168.1 (C1), 159.2 (C3), 134.3, 129.7 (C10, C11), 117.6 (C2), 71.1 (C13), 70.0 (C7), 67.4 (C6), 65.0 (C16), 60.3 (OCH$_2$CH$_3$), 44.7 (C12), 40.8 (C8), 35.5 (C4), 32.3 (C9), 27.1 (C15), 20.2 (C14), 16.5 (C17), 14.1 (OCH$_2$CH$_3$).

EXAMPLE 6

Monic Acid C

Monic acid A (3.44 g) was dissolved in 2,2-dimethoxypropane (30 ml) and ethyl acetate (30 ml) with a few crystals of p-toluene sulphonic acid. After one hour the solution was diluted with ethyl acetate and washed with brine then dried (MgSO$_4$). The solvent was removed in vacuo and the acetonide dissolved in water-methanol (1:1, 40 ml) then treated with potassium bicarbonate (1.0 g, 1 eq). The solution was evaporated to dryness and potassium selenocyanate (4.32 g, 3 eq), tert-amyl alcohol-water (9:1, 150 ml) added and reaction refluxed for 42 hours. After filtering, the reaction mixture was diluted with ethyl acetate and extracted with water (4×25 ml). The combined aqueous phases were acidified (pH2, 5 M-HCl) and extracted with ethyl acetate (4×25 ml) and the combined extracts dried (MgSO$_4$). The solvent was removed in vacuo to give 6,7-O-ispropylidene monic acid C, $\nu_{max}$ (CHCl$_3$) 1695, 1640, 1380, 1370, 1220 and 1055 cm$^{-1}$; $\delta_H$(CDCl$_3$) 0.98 (3H, d, CH$_3$-17), 1.13 (3H, d, CH$_3$-14), 1.33 and 1.48 (6H, d, acetonide C$\underline{H}_3$'s), 2.17 (3H, s, CH$_3$-15), 5.45 (2H, m, H-10, H-11), 5.75 (1H, s, H-2), 4.35 (2H, broad, CO$_2$H, OH); $\delta_C$ (CDCl$_3$) 170.5 (C1), 158.3 (C3), 134.9, 128.8 (C10, C11), 117.5 (C2),

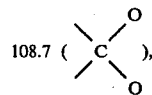

108.7 ( 76.5 (C5), 75.7 (C7), 74.1 (C6), 71.1 (C13), 66.5 (C16), 44.3 (C12), 36.8 (C8), 34.1 (C9), 28.3, 26.3 (C(CH$_3$)$_2$), 20.1 (C14), 19.3 (C15), 16.3 (C17); m/e (relative intensity) 353 (9) (Found: 353.1995. M$^+$—CH$_3$ requires 353.2026) 350 (4) (M$^+$—H$_2$O). The acetonide was dissolved in 80% acetic acid (100 ml) then left overnight. The solution was evaporated to dryness and chromatographed on silica (50 g) eluting with 0–10% methanol-chloroform. The fractions containing pure product (tlc) were combined and evaporated to give monic acid C m.p. 101°–102° C. (2.57 g, 72%) (Found: C, 61.8; H, 8.4. C$_{17}$H$_{28}$O$_6$ requires C, 62.2; H, 8.6%).

EXAMPLE 7

Ethyl Monate C

Ethyl monate A (5 g), potassium selenocyanate (5.8 g) in 2-ethyl-n-butanol/water (9:1, 175 ml) were refluxed for 2 days. The reaction mixture was then filtered and evaporated to an oil which was dissolved in ethyl acetate, washed with brine then dried (MgSO$_4$) and evaporated. The residual oil was chromatographed on silica (50 g) eluting with 0–6% methanol-chloroform. The pure fractions (tlc) were combined and evaporated to give ethyl monate C (2.46 g, 51%) m.p. 96°–97° C.

EXAMPLE 8

Allyl Monate C

Allyl monate A (500 mgs), potassium selenocyanate in 2-ethyl-n-butanol/water (9:1, 15 ml) were refluxed for 24 hours. The reaction mixture was then filtered and the filtrate evaporated to dryness and the residue dissolved in ethyl acetate (20 ml) and brine (20 ml). The organic layer was separated and washed with brine (20 ml) then dried (MgSO$_4$) and the solvent evaporated in vacuo. The resultant oil was chromatographed on silica (8 g) eluting with 0–6) methanol/chloroform. Fractions containing pure product were combined and evaporated to an oil which crystallised m.p. 87°–89° C. (39 mgs, 8%), $\nu_{max}$ (CHCl$_3$) 3400 (broad), 1703, 1642, 1210, 1045 and 909 cm$^{-1}$, $\lambda_{max}$ (EtOH) 222 nm ($\epsilon$14600); $\delta_H$ (CDCl$_3$) 0.97 (3H, d, J 7 Hz, C17-C$\underline{H}_3$), 1.13 (3H, d, J 7 Hz, C17-C$\underline{H}_3$), 2.19 (3H, s, C15-C$\underline{H}_3$), 6.56 (2H, m, OC$\underline{H}_2$CH═CH$_2$), $\delta_C$ (CDCl$_3$) 166.4 (C1), 157.7 (C3), 134.4, 129.3 (C10, C11), 132.6, 117.9 (CH═CH$_2$), 117.2 (C2), 74.9 (C5), 71.3 (C13), 70.3 (C7), 68.9 (C6), 64.9 (C16), 64.5 (CH$_2$CH═CH$_2$), 44.6 (C12), 43.1 (C4), 42.0 (C8), 32.4 (C9), 20.4 (C14), 19.3 (C15), 16.6 (C17) (Found: C, 65.0; H, 8.4. C$_{20}$H$_{32}$O$_6$ requires C, 65.2; H, 8.7%).

EXAMPLE 9

6-Hydroxyhexyl Monate C

Monic acid C (328 mgs) was dissolved in methanol-water (1:1, 20 ml) and sodium bicarbonate (81 mgs, 1 eq) added. The solution was evaporated to dryness and dissolved in dimethylformamide (20 ml)/hexamethyl phosphoramide (few drops) and 1-chloro-6-hydroxyhexane (0.34 ml, 3 eq) and sodium iodide (150 mgs, 1 eq) added. The reaction was stirred at 80° C. overnight then the solvent evaporated under reduced pressure and the residue dissolved in ethyl acetate (20 ml)/brine (20 ml). After separation of the organic phase the aqueous layer was further extracted with ethyl acetate (20 ml) and dried (MgSO$_4$). The solvent was evaporated and the residual oil chromatographed on silica (10 g) eluting with 0–6% methanol/chloroform. Fractions containing pure product were combined and evaporated to give (227 mg, 50%), $\nu_{max}$ (CHCl$_3$), 3420 (broad), 1700, 1642, 1220, 1152 and 1050 cm$^{-1}$, $\lambda_{max}$ (EtOH) 220 nm ($\epsilon$m 11,600); $\delta_H$ (CDCl$_3$) 0.98 (3H, d, CH$_3$-17), 1.15 (3H, d, CH$_3$-14), 1.44 (6H, m, (CH$_2$)$_3$), 2.19 (3H, s, CH$_3$-15), 4.07 (2H, t, CO$_2$CH$_2$), 5.45 (2H, m, H-10, H-11), 5.75 (1H, S, H-2), $\delta_C$ (CDCl$_3$) 167.0 (C1), 157.3 (C3), 134.4, 129.1 (C10, C11), 117.4 (C2), 74.8 (C5), 71.2 (C13), 70.3 (C7), 68.8 (C6), 64.8 (C16), 63.7 (C1'), 62.4 (C6'), 44.4 (C12), 43.1 (C4), 32.4 (C9, C4'), 28.6, 25.8, 25.4 (C3', C4', C5'), 20.3 (C14), 19.2 (C15), 16.5 (C17); m/e (relative intensity) 428 (2) (Found: 428.2797. M$^+$ requires 428.2820), 384 (7), 266 (43%), (C.I., NH$_3$) 429 (M+ +H), 446 (M+ +NH$_4$).

EXAMPLE 10

Isobutyl Monate C

Sodium monate C (350 mgs) was dissolved in dimethylformamide (20 ml) and hexamethylphosphoramide (few drops) then treated with sodium iodide (150 mg, 1 eq) and isobutyl bromide (0.54 ml, 5 eq). The solution was heated at 80° C. overnight then the solvent removed under reduced pressure. The residue was dissolved in ethylacetate (20 ml)/brine (20 ml) and the organic layer separated, washed with brine then dried (MgSO$_4$). Removal of the solvent afforded an oil which was chromatographed on silica (7 g) eluting with 0–4% methanol/chloroform. Fractions containing pure product were combined and evaporated to give the desired product (330 mg, 86%), $\nu_{max}$ (CHCl$_3$) 3400 (broad), 1700 and 1642 cm$^{-1}$, $\lambda_{max}$ (EtOH) 219 nm ($\epsilon$m 10,900); $\delta_H$ (CDCl$_3$) 0.95 (6H, d, CH(CH$_3$)$_2$), 0.97 (3H, d, CH$_3$-17), 1.13 (3H, d, CH$_3$-14), 2.18 (3H, s, CH$_3$-15), 3.85 (2H, d, CO$_2$CH$_2$), 5.45 (2H, m, H-10, H-11), 5.78 (1H, s, H-2); $\delta_C$ (CDCl$_3$) 166.9 (s) (C1) 157.4 (s) (C3), 134.4 (dd), 129.0 (dd) (C10, C11), 117.4 (d) (C2), 75.0 (d) (C5), 71.1 (d) (C13), 70.4 (d) (C7), 69.9 (t) (C1'), 68.9 (d) (C6), 64.8 (t) (C16), 44.3 (d) (C12), 43.2 (t) (C4), 42.1 (d) (C8), 32.5 (t) (C9), 27.8 (d) (C2'), 20.2 (q) (C14), 19.2 (q, q×2) (C15, C3'×2), 16.3 (q) (C17); m/e (relative intensity) 384 (1) (Found: 384.2527 M+ requires 384.2542), 360 (13), 306 (9), 252 (62).

BIOLOGICAL DATA

(a) Human Bacteria

Table 1 shows the MIC values ($\mu$g/ml) of a number of esters of monic acid C (i.e. compound (II) in which the tri-substituted double bond in the E-configuration) against a number of organisms important in human infections obtained by serial dilution in nutrient agar.

TABLE 1

| | MIC of Ester of Monic Acid C | | | | |
|---|---|---|---|---|---|
| Organism | Methyl | Ethyl | Iso-Butyl | Allyl | 6-hydroxy-hexyl |
| Past. multocida 1633 | 10.0 | 5.0 | 5.0 | 2.5 | 1.0 |
| H. influenzae 01 | 1.0 | 0.2 | 1.0 | 0.5 | 0.2 |
| H. influenzae Wy21 | 2.5 | 1.0 | 1.0 | —0.2 | |
| N. catarrhalis 1502 | 1.0 | 0.2 | 1.0 | 0.05 | — |
| B. subtilis | 2.5 | 1.0 | 1.0 | 1.0 | 0.5 |
| Staph. aureus Oxford | 1.0 | 0.2 | 0.5 | 0.1 | 0.2 |
| Staph. aureus Russell | 2.5 | 0.2 | 1.0 | 1.0 | 1.0 |
| Staph. aureus 1517 | 2.5 | 0.2 | — | — | — |
| Strep. pyogenes A 64/848 | >100.0 | 10.0 | 10 | 2.5 | 1.0 |
| Strep. pyogenes B 2788 | 25.0 | 0.5 | 25 | 2.5 | 5.0 |
| Strep. pyogenes C 2761 | >100.0 | 5.0 | 25 | 10 | 5.0 |
| Strep. pneumoniae CN33 | 25.0 | 2.5 | 5.0 | 2.5 | — |

(b) Veterinary Bacteria

Table 2 shows the MIC values ($\mu$g/ml) of a number of esters of monic acid C against a number of organisms important in veterinary infections.

TABLE 2

| | Ester of Monic Acid C | | | |
|---|---|---|---|---|
| Organism | Ethyl | Isobutyl | Allyl | 6-Hydroxy-hexyl |
| Bord. bronchiseptica BO8 | >80 | >80 | >80 | >80 |
| Bord. bronchiseptica BO9 | 40 | 40 | 40 | 5 |
| Past. multocida PA1 | 5 | 10 | 2.5 | 2.5 |
| Past. multocida PA2 | 5 | 10 | 0.312 | 2.5 |
| Past. haemolytica PA5 | 40 | 80 | 20 | 40 |
| Staph. aureus B4 (pen resistant) | 1.25 | 1.25 | 0.625 | 1.25 |
| Staph. aureus 152 (pen sensitive) | — | 1.25 | 0.625 | 1.25 |
| Strep. uberis SPU1 | 5 | 1.25 | 1.25 | 0.312 |
| Strep. dysgalactiae SPD1 | 20 | 5 | 5 | 1.25 |
| Strep. agalactiae SPA1 | 20 | 10 | 5 | 5 |

(c) Anti-Mycoplasma Activity

Table 3 shows MIC values ($\mu$g/ml) of a number of esters of monic acid C against a number of mycoplasma organisms, determined either in broth (Friis' broth using microtiter method) or in agar (by serial dilution in Friis' agar).

TABLE 3

| | Ester of Monic Acid C | | | |
|---|---|---|---|---|
| | Methyl | | Ethyl | |
| Organism | Broth | Agar | Broth | Agar |
| 1 M. suipneumoniae Str. 11 | 2.5 | | 1.25 | |
| 2 M. suipneumoniae J2206/183b | 2.5 | | 10 | |
| 3 M. dispar H225 | 0.625 | | 0.078 | |
| 4 M. dispar NCTC 10125 | 0.312 | | 0.156 | |
| 5 M. pneumoniae 427a | >10 | >10 | 10 | 5.0 |
| 6 M. pneumoniae ATCC 15492 | 10 | >10 | 10 | 5.0 |
| 7 M. bovis ATCC 25025 | — | 0.312 | — | 0.156 |
| 8 M. bovis NCTC 10131 | — | 0.312 | — | 0.156 |
| 9 M. fermentans MWKL4 | 0.312 | 0.625 | 0.156 | 0.312 |
| 10 M. pulmonis JB | 0.156 | 0.312 | 0.156 | 0.039 |
| 11 M. hyorhinis ATCC 23234 | | 1.25 | | 2.5 |
| 12 M. hyosynoviae ATCC 25591 | | 5.0 | | 1.25 |
| 13 M. arthritidis ATCC 14124 | | >10 | | >10.0 |
| 14 M. gallisepticum S6 | | >10 | | >10.0 |
| 15 M. synoviae ATCC 25204 | | 0.156 | | 0.039 |
| 16 M. alkalescens NCTC 10135 | | 0.156 | | 0.039 |
| 17 M. bovigenitalium ATCC 14173 | | 0.156 | | 0.078 |

| | Ester of Monic Acid C | | | | | |
|---|---|---|---|---|---|---|
| | Isobutyl | | Allyl | | 6-Hydroxyhexyl | |
| | Broth | Agar | Broth | Agar | Broth | Agar |
| 1 | 1.25 | | 0.312 | | 0.625 | |
| 2 | 1.25 | | 1.25 | | 1.25 | |
| 3 | 0.312 | | 0.078 | | 0.156 | |
| 4 | 0.312 | | 0.156 | | 0.156 | |
| 5 | 1.25 | 10 | 10 | 5 | 0.625 | 1.25 |
| 6 | 2.5 | 10 | 10 | 10 | 0.625 | 1.25 |
| 7 | — | 0.156 | — | 0.078 | — | <0.02 |
| 8 | — | 0.156 | — | 0.078 | — | <0.02 |
| 9 | 0.039 | 0.312 | 0.039 | 0.156 | <0.02 | 0.078 |
| 10 | <0.02 | 0.078 | 0.039 | 0.156 | <0.02 | 0.039 |
| 11 | | 2.5 | | 2.5 | | 1.25 |
| 12 | | 0.625 | | 1.25 | | 0.078 |
| 13 | | 5.0 | | >10 | | 5.0 |
| 14 | | >10 | | >10 | | 10 |
| 15 | | 0.078 | | 0.039 | | <0.02 |
| 16 | | 0.156 | | 0.078 | | <0.02 |
| 17 | | 0.078 | | 0.078 | | 0.039 |

We claim:
1. A compound of formula

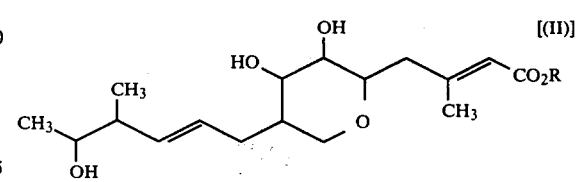

wherein R is hydrogen or a salt-forming cation.

* * * * *